(12) United States Patent
Liu et al.

(10) Patent No.: US 6,693,206 B2
(45) Date of Patent: Feb. 17, 2004

(54) HYDROLYTIC KINETIC RESOLUTION OF EPOXIDES

(75) Inventors: Yi Liu, Weymouth, MA (US); Marcello DiMare, Belmont, MA (US); Salvatore Anthony Marchese, Malden, MA (US); Eric N. Jacobsen, Boston, MA (US); Serge Jasmin, Watertown, MA (US)

(73) Assignee: Rhodia Chirex, Inc., MA (US)

( * ) Notice: Subject to any disclaimer, the term of this patent is extended or adjusted under 35 U.S.C. 154(b) by 11 days.

(21) Appl. No.: 10/225,869

(22) Filed: Aug. 22, 2002

(65) Prior Publication Data

US 2003/0073855 A1 Apr. 17, 2003

Related U.S. Application Data

(60) Provisional application No. 60/314,247, filed on Aug. 22, 2001.

(51) Int. Cl.$^7$ .............................................. C07D 301/32
(52) U.S. Cl. ...................... 549/541; 549/513; 549/540
(58) Field of Search .............................. 549/541, 513, 549/540

(56) References Cited

U.S. PATENT DOCUMENTS

| | | | |
|---|---|---|---|
| 5,637,739 A | 6/1997 | Jacobsen et al. | 549/524 |
| 5,663,393 A | 9/1997 | Jacobsen et al. | 556/45 |
| 5,665,890 A | 9/1997 | Jacobsen et al. | 549/230 |
| 5,929,232 A | 7/1999 | Jacobsen et al. | 540/145 |
| 6,262,278 B1 | 7/2001 | Jacobsen et al. | 549/230 |

FOREIGN PATENT DOCUMENTS

| | | | |
|---|---|---|---|
| WO | WO 01/89690 | 11/2001 | B01J/31/00 |

OTHER PUBLICATIONS

Jacobsen, "Asymmetric Catalysis of Epoxide Ring–Opening Reactions." Acc. Chem. Res. 2000, 33, 421–431.

Annis et al, "Polymer–supported chiral Co(Salen) complexes: Synthetic applications and mechanistic investigations in the hydrolytic kinetic resolution of terminal epoxides." J. Am. Chem. Soc., 121, 4147–4154 (1999).

Ready et al, "Asymmetric catalytic synthesis of a–aryloxy alcohols: kinetic resolution of terminal epoxides via highly enantioselective ring–opening with phenols." J. Am. Chem. Soc. 1999, 121, 6086–6087.

Ready et al, "Highly active oligomeric (salen)Co catalysts for asymmetric epoxide ring–opening reactions." J. Am. Chem. Soc. 2001, 2687–2688.

Furrow et al, "Practical access to highly enantioenriched C–3 building blocks via hydrolytic kinetic resolution." J. Org. Chem. 1998, 63, 6776–6777.

Ready et al, "A practical oligomeric [(salen)Co] catalyst for asymmetric epoxide ring–opening reactions." Agnew Chem. Int. Ed. 2002, 41, No. 8, 1374–1377.

Document No. 115:8638, Narasaka et al. (1991) "Asymetric Diels–Alder reactions of an acrylic acid derivative using a chiral titanium catalyst", Bulletin of the Chemical Society of Japan, 64(2), pp. 387–391.

Stinson, Stephen C., *Chem. Eng. News*, pp. 46–79, Sep. 28, 1992.

*Primary Examiner*—Ba K. Trinh
(74) *Attorney, Agent, or Firm*—Ohlandt, Greeley, Ruggiero & Perle, L.L.P.

(57) ABSTRACT

The present invention provides a process for the preparation of an enantiomerically enriched non-racemic chiral diol and an enantiomerically enriched non-racemic chiral epoxy compound by a hydrolytic kinetic resolution reaction. The process includes the step of contacting oxygen and mixture including a racemic chiral epoxy compound, a non-racemic Co(II) complex catalyst, an aromatic carboxylic acid and water, at a temperature and length of time sufficient to produce a mixture of said non-racemic chiral diol and said non-racemic chiral epoxy compound. The present invention also provides a process for the preparation of an enantiomerically enriched non-racemic chiral diol and an enantiomerically enriched non-racemic chiral epoxy compound by a hydrolytic kinetic resolution reaction. This process includes the step of: contacting a racemic chiral epoxy compound and water in the presence of a non-racemic complex of Co(III) having an aryl carboxylate counter-anion, at a temperature and length of time sufficient to produce a mixture of said non-racemic chiral diol and said non-racemic chiral epoxy compound.

56 Claims, No Drawings

HYDROLYTIC KINETIC RESOLUTION OF EPOXIDES

This application claims priority from Provisional Application Serial No. 60/314,247 filed on Aug. 22, 2001.

BACKGROUND OF THE INVENTION

1. Field of the Invention

The present invention relates to an improved process for hydrolytic kinetic resolution (HKR) of epoxides. More particularly, the present invention relates to an improved process for the preparation of non-racemic compounds using as a promoter a carboxylic acid, such as, electron deficient aromatic acid, activation of the catalyst with epoxides present and the use ammonium hydroxide during work-up.

2. Description of the Prior Art

The demand for enantiomerically pure compounds or non-racemic compounds having high optical purity, i.e., having an optical purity of at least 85% enantiomeric excess, has grown rapidly in recent years. The impetus for rapid growth has been the potential uses of such compounds as biologically active compounds or as intermediates in the synthesis of such biologically active compounds, particularly in the pharmaceutical and agrochemical industries.

It has become increasingly clear that enantiomerically pure drugs have numerous advantages over racemic drug mixtures including advantages, such as, fewer side effects and greater potency, which result in part from the ability of living systems to differentiate between enantiomeric compounds. Some of these advantages are summarized in a review article in *Chem. Eng. News*, pp. 46–79, Sep. 28, 1992.

U.S. Pat. No. 5,665,890 to Jacobsen et al. describes a stereoselective chemical synthesis by the reaction of a nucleophile and a chiral or prochiral cyclic substrate, such as an epoxide, in the presence of a non-racemic chiral catalyst, such as, chiral Co(salen)-catalyzed ring-opening reactions of racemic or enantiopure epoxides with nucleophiles.

U.S. Pat. No. 5,929,232, also to Jacobsen et al., describes a kinetic resolution of a cyclic substrate, such as an epoxide, in the presence of a non-racemic chiral catalyst.

U.S. Pat. Nos. 5,663,393 and 5,637,739, both to Jacobsen et al., describe catalysts that are useful in the above stereoselective chemical syntheses and kinetic resolution reactions.

Various aspects of kinetic resolution reactions, including ring opening of epoxides with nucleophiles has been mentioned by the following references: Annis and Jacobsen, *J. Am. Chem. Soc.*, 121, 4147–4154 (1999); Ready and Jacobsen, *J. Am. Chem. Soc.*, 121, 6086–6087 (1999); Jacobsen, *Acc. Chem. Res.* 2000, 33, 421–431; and Tokunaga, Larrow, Kakiuchi, and Jacobsen, *Science* 1997, 277, 936–938.

Existing hydrolytic kinetic resolution (HKR) technology requires pre-activation of the catalyst precursor, such as, Co(II)(salen), the structure of which is shown in Example 1, in dichloromethane with acetic acid promoter for 1 to 2 hours in the presence of air. The dichloromethane is then removed from the Co(III)(salen) catalyst, and the epoxide is added, followed by careful dosing of water. When the reaction is complete, the epoxide product is separated from the diol product by distillation.

Problems associated with the above process include the following:

(1) a separate catalyst activation step is required, the use of dichloromethane requires special equipment and additional expenses for handling and disposal and the exchange of dichloromethane for epoxide takes a significant amount of processing time;

(2) the process has moderate repeatability due to the use of a volatile and relatively reactive promoter, such as, acetic acid, which produces results that have poor reproducibility;

(3) the process has moderate efficiency due to high catalyst load required, which ranges from 0.2 mol % to 2 mol %, depending upon the epoxide; and (4) the product is difficult to separate because the combination of heat and the presence of Co(II)(salen) during distillation can erode the enantiomeric excess of the epoxide, i.e., the epoxide can be entrained in the diol during distillation, leading to lower isolated yields of the high optical purity or enantiopure epoxide.

Thus, a more efficient catalyst activation method, better promoters, new separation techniques to isolate optically pure epoxide from diol, and a means of lowering Co(II)(salen) levels during work-up are very desirable.

None of the above references addresses these problems or provides a solution thereof. None of the above references discloses the preparation of non-racemic products using electron deficient aromatic acids as promoters, activation of the catalyst with epoxides present and the use of ammonium hydroxide during work-up.

Accordingly, the present invention provides a process for the preparation of enantiomerically pure epoxides or non-racemic epoxides and corresponding diols having high optical purity, i.e., having an optical purity of at least 85% enantiomeric excess, which can be useful as intermediate in the synthesis of a variety of widely used pharmaceutical and other products.

SUMMARY OF THE INVENTION

The present invention provides a process for the preparation of an enantiomerically enriched non-racemic chiral diol and an enantiomerically enriched non-racemic chiral epoxy compound by a hydrolytic kinetic resolution reaction. The process includes the step of contacting oxygen and mixture including a racemic chiral epoxy compound, a non-racemic Co(II) complex catalyst, an aromatic carboxylic acid and water, at a temperature and length of time sufficient to produce a mixture of the non-racemic chiral diol and the non-racemic chiral epoxy compound.

The present invention further provides a process for the preparation of an enantiomerically enriched non-racemic chiral diol and an enantiomerically enriched non-racemic chiral epoxy compound by a hydrolytic kinetic resolution reaction. The process includes the step of: contacting a racemic chiral epoxy compound and water in the presence of a non-racemic complex of Co(III) having an aryl carboxylate counter-anion, at a temperature and length of time sufficient to produce a mixture of the non-racemic chiral diol and the non-racemic chiral epoxy compound.

The present invention still further provides a process for the preparation of an enantiomerically enriched non-racemic chiral diol and an enantiomerically enriched non-racemic chiral epoxy compound by a hydrolytic kinetic resolution reaction, including the step of:

contacting: (a) oxygen and a mixture including a racemic chiral epoxy compound, a non-racemic Co(II) complex catalyst, an aromatic carboxylic acid and water; or (b) a racemic chiral epoxy compound and water in the presence of a non-racemic complex of Co(III) having an aryl carboxylate counter-anion; wherein the contacting is carried out at a temperature and length of time sufficient to produce a mixture of the non-racemic chiral diol and the non-racemic chiral epoxy compound;

contacting the mixture and a nitrogenous base to produce a solution of the mixture; and washing the solution of the mixture with water to separate the non-racemic chiral diol from the non-racemic chiral epoxy compound as an aqueous solution thereof.

The present invention also provides a process for the preparation of an enantiomerically enriched non-racemic chiral diol and an enantiomerically enriched non-racemic chiral epoxy compound by a hydrolytic kinetic resolution reaction. The process includes the steps of:

contacting oxygen and a mixture comprising a racemic chiral epoxy compound, a non-racemic Co(II) complex catalyst, a carboxylic acid and water, at a temperature and length of time sufficient to produce a mixture of said non-racemic chiral diol and said non-racemic chiral epoxy compound; and contacting said mixture and a nitrogenous base to produce a solution of said mixture.

Lastly, the present invention provides a process for the preparation of an enantiomerically enriched non-racemic chiral diol and an enantiomerically enriched non-racemic chiral epoxy compound by a hydrolytic kinetic resolution reaction. The process includes the steps of:

contacting a racemic chiral epoxy compound and water in the presence of a non-racemic complex of Co(III) having an a carboxylate counter-anion, at a temperature and length of time sufficient to produce a mixture of said non-racemic chiral diol and said non-racemic chiral epoxy compound; and contacting said mixture and a nitrogenous base to produce a solution of said mixture.

The present also provides a non-racemic chiral epoxy compound and a diol having a high regioselectivity and enantioselectivity prepared by a processes according to the present invention.

The advantage of the present process include the following:

(1) activation of the catalyst can be achieved in the presence of the epoxide;

(2) the use of dichloromethane is avoided;

(3) the processing time can be substantially reduced;

(4) a lower catalyst load is needed to achieve highly enantiomerically enriched epoxides and diols by using, preferably, electron-deficient aromatic acids as promoter;

(5) the process has better reproducibility;

(6) the use ammonium hydroxide as an additive during work-up at the end of the reaction, converts the Co(II) (salen) catalyst to a more stable Co(III)(salen) ammonia complex, which erodes the ee of product epoxide much slower than the catalyst precursor; and (7) Co(III)(salen) ammonia complex is substantially more soluble than its precursor, the Co(II)(salen) catalyst, which allows the removal of the diol product by extraction into the water layer.

DETAILED DESCRIPTION OF THE INVENTION

The hydrolytic kinetic resolution (HKR) of epoxides has used to produce highly enantiomerically enriched epoxides and diols as pharmaceutical intermediates. The present invention provides a process in which (1) the catalyst used in the hydrolytic kinetic resolution (HKR) can be activated in the presence of the epoxide, (2) the efficiency of the hydrolytic kinetic resolution (HKR) can improved by using electron-deficient aromatic acids as promoters, and (3) the isolation of the product can improved by use of ammonium hydroxide during work-up.

In one aspect, the process of the present invention permits the preparation of an enantiomerically enriched non-racemic chiral diol and an enantiomerically enriched non-racemic chiral epoxy compound by the improved hydrolytic kinetic resolution reaction according to the present invention. The process includes the step of contacting oxygen and a mixture including a racemic chiral epoxy compound, a non-racemic Co(II) complex catalyst, an aromatic carboxylic acid and water.

The racemic chiral epoxy compound can be any suitable epoxide. Preferably, the racemic chiral epoxy compound is represented by the formula:

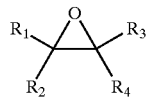

wherein each $R^1$, $R^2$, $R^3$ and $R^4$ can independently be hydrogen, halogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, acyl, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, two or more of $R^1$, $R^2$, $R^3$ and $R^4$ together can form a carbocyclic or heterocyclic 4 to 8 membered ring, or any combination thereof.

Particularly preferred are racemic chiral epoxy compounds that have one or more of $R^1$, $R^2$, $R^3$ and $R^4$ represented by the formula:

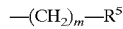

wherein $R^5$ can independently be alkyl, cycloalkyl, cycloalkenyl, aryl, heteroaryl and heterocycle; and wherein m is zero or an integer from 1 to 8.

Examples of such racemic chiral epoxy compounds include styrene oxide, propylene oxide, methyl glycidate, epichlorohydrin and a mixture thereof.

The catalyst can be a salt, such as, an inorganic salt, or is a chiral complex of a metal with suitable ligand. Suitable metals include: Co(II), Co(III), Mg(II), Zn(II), Al(III), Sc(III), Zr(IV), Ti(IV), Sn (II or IV), La(III), Yb(III) and Ce(III). Suitable ligands include oxygen, nitrogen, sulfur, phosphorus and carbon based monodentate, bidentate, tridentate or tetradentate ligands. Particularly preferred ligands are "salen" ligands disclosed in the previously mentioned U.S. Pat. Nos. 5,665,890, 5,929,232, 5,663,393 and 5,637,739, all to Jacobsen et al.

The preferred non-racemic Co(II) complex catalysts include the (S,S)-Co(II)(salen) catalyst and (R,R)-Co(II)(salen) catalyst, respectively represented by the formulae:

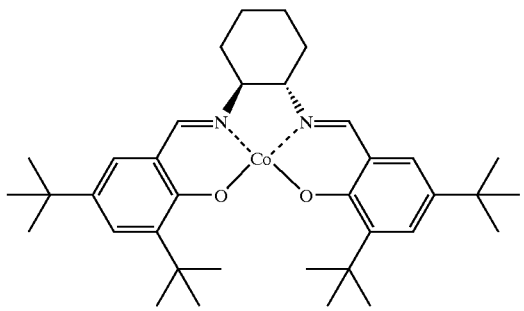

(S,S)-Co(salen)

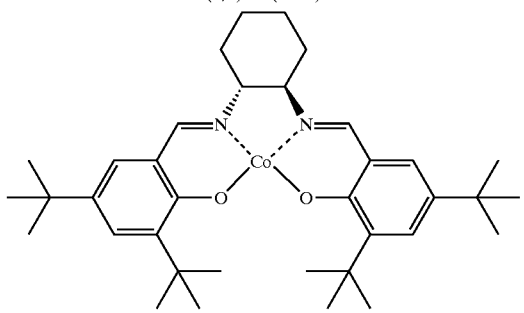

(R,R)-Co(Salen)

In the presence of oxygen, the non-racemic complex of Co(II) produces a non-racemic complex of Co(III) having an aryl carboxylate counter-anion under the reaction conditions of the process of the present invention. Thus, under the reaction conditions of the present process, the active form of the catalyst is the non-racemic complex (S,S)-Co(III)(salen)(arylcarboxylate) or (R,R)-Co(III)(salen)(arylcarboxylate).

The carboxylate counter-anion in the Co(III)(salen)-(carboxylate) catalysts can be a substituted or unsubstituted alkyl or aryl carboxylate. Aryl carboxylates that are substituted with electron withdrawing groups to produce electron deficient carboxylates are preferred.

The arylcarboxylate counter-anion in the Co(III)(salen)-(arylcarboxylate) catalysts derived from an aromatic carboxylic acid, which can be represented by the formula:

Ar—COOH wherein Ar is a substituted aromatic group of 1 to 24 carbon atoms having one or more substituents. Preferably, each of the substituents can be hydrogen, halogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, haloalkyl, haloalkenyl, haloalkynyl, heterocyclic group of 2 to 7 carbon atoms containing one or more of oxygen, nitrogen or sulfur, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, nitro, fluoro, cyano, acyl, imine, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, tertiary amine cation or a combination thereof.

Preferably, the substituted aromatic group is an electron deficient substituted aromatic group having one or more electron withdrawing substituents, such as, nitro, fluoro, chloro, bromo, cyano, acyl, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation, or a combination thereof.

Examples of suitable aromatic carboxylic acids include nitrophenyl, dinitrophenyl, trinitrophenyl, chlorophenyl, dichlorophenyl, trichlorophenyl, tetrachlorophenyl, pentachlorophenyl, fluorophenyl, difluorophenyl, trifluorophenyl, tetrafluorophenyl, pentafluorophenyl, cyanophenyl, dicyanophenyl, tricyanophenyl and a combination thereof.

Particularly preferred are aromatic carboxylic acids represented by the formula:

$R^6$—$C_6H_4$—COOH wherein $R^6$ can be nitro, fluoro, chloro, cyano, acyl, alkoxycarbonyl, aryloxycarbonyl, aminocarbonyl, alkanesulfonyl, arylsulfonyl, perfluoroalkanesulfonyl, perfluoroarylsulfonyl, tertiary amine cation or a combination thereof.

It would be evident to those skilled in the art that the above aromatic acids can be generated in-situ.

The process of the present invention further includes the step of contacting the reaction mixture and a nitrogenous base to produce a solution of the mixture. The nitrogenous base can be an amine, an amidine, a guanidine, imidate ester, ammonium hydroxide, hydroxyamine and a combination thereof. Suitable amines can be represented by the formula:

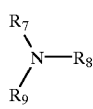

wherein each $R^7$, $R^8$ and $R^9$ can independently be hydrogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, hydroxyalkyl, aminoalkyl, alkylaminoalkyl, dialkylaminoalkyl, aminoaryl, alkylaminoaryl, dialkylaminoaryl, trialkylsilyl, alkyl ether, aryl ether, alkyl aryl ether, two or more of $R^7$, $R^8$ and $R^9$ together form a carbocyclic or heterocyclic 4 to 8 membered ring, or a combination thereof. Preferably, the base is ammonium hydroxide.

The process of the present invention further includes the step of washing the solution of the mixture with water to separate the non-racemic chiral diol from the non-racemic chiral epoxy compound as an aqueous solution. Thereafter, the non-racemic chiral epoxy compound can be distilled to produce the enantiomerically enriched non-racemic chiral epoxy compound in high regioselectivity and enantioselectivity. The enantiomerically enriched non-racemic chiral diol can be obtained in high regioselectivity and enantioselectivity by concentrating the aqueous solution of the non-racemic chiral diol by known methods, such as, evaporation under reduced pressure.

Thus, the present process provides non-racemic chiral epoxy compounds and a diols having a high regioselectivities and enantioselectivities. Examples of the non-racemic chiral epoxy compounds that can be prepared by the present process include compounds represented by the formulae:

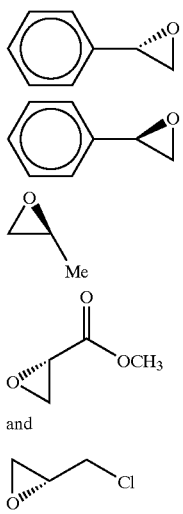

Examples of the non-racemic chiral diols include compounds represented by the formulae:

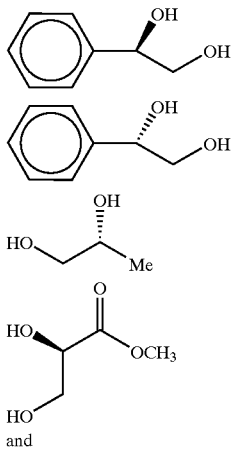

-continued

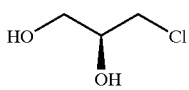

In another aspect, the process of the present invention permits the preparation of an enantiomerically enriched non-racemic chiral diol and an enantiomerically enriched non-racemic chiral epoxy compound by a hydrolytic kinetic resolution reaction by a process, which includes the step of contacting a racemic chiral epoxy compound and water in the presence of a non-racemic complex of Co(III) which has an aryl carboxylate counter-anion. This process can be practiced either in the presence of oxygen or in the absence of oxygen.

The racemic chiral epoxy compound can be any of the epoxides previously described above. However, the catalyst in this embodiment is the non-racemic complex of Co(III) having an aryl carboxylate counter-anion, such as, (S,S)-Co(III)(salen)-(arylcarboxylate) and (R,R)-Co(III)(salen)-(arylcarboxylate) catalysts.

As described above, the arylcarboxylate counter-anion in the Co(III)(salen)-(arylcarboxylate) catalysts derived from an aromatic carboxylic acid is represented by the formula:

wherein Ar is a substituted aromatic group of 1 to 24 carbon atoms having one or more substituents, which preferably are electron deficient substituents.

The contacting step is typically carried out at or near room temperature, from about 1 hour to about 48 hours, preferably overnight. These conditions are generally sufficient for completion of the reaction and produce a mixture of the non-racemic chiral diol and the non-racemic chiral epoxy compound in high yield.

In this embodiment, the process can further include the step of contacting the reaction mixture and a nitrogenous base, such as, an amine, an amidine, a guanidine, an imidate ester, ammonium hydroxide, hydroxyamine or a combination thereof, to produce a solution of the mixture. The process can also include the step of washing the solution of the mixture with water to separate the non-racemic chiral diol from the non-racemic chiral epoxy compound as an aqueous solution. After the washing step, the non-racemic chiral epoxy compound can be distilled to produce the enantiomerically enriched non-racemic chiral epoxy compound in high regioselectivity and enantioselectivity. The enantiomerically enriched non-racemic chiral diol can be obtained in high regioselectivity and enantioselectivity by concentrating the aqueous solution of the non-racemic chiral diol by known methods, such as, evaporation under reduced pressure.

In still another aspect, after the step of contacting: (a) oxygen and a mixture including a racemic chiral epoxy compound, a non-racemic Co(II) complex catalyst, an aromatic carboxylic acid and water or (b) a racemic chiral epoxy compound and water in the presence of a non-racemic complex of Co(III) having an aryl carboxylate counter-anion, the steps of: (1) contacting the reaction mixture and a nitrogenous base, (2) washing the solution of the mixture with water, (3) distilling the non-racemic chiral epoxy compound and (4) concentrating the aqueous solution of non-racemic chiral diol can be combined to produce the enantiomerically enriched non-racemic chiral diol in high regioselectivity and enantioselectivity.

Additional elements also deemed important include: ranges of catalyst equivalents from 0.1 to 50 mol %, with 0.1 to 1 mol % representing the preferred embodiment; reactions run neat or with solvents, chosen from ethers (tert-butyl methyl ether as an example), alcohols (isopropyl alcohols as an example), diols (1,2-propylene glycol as an example), mono ethers of diols (1-methoxy-2-propanol as an example), aromatic solvents (toluene as an example), and halogenated solvents (such as dichloromethane, and polyfluoro-alkanes);

Ranges of catalyst equivalents are from 0.01 to 5 mol %, based on the epoxide, with 0.1 to 2 mol % being preferred. Water is from 50 to 5000 mol %, based on the epoxide, with 50 to 200 mol % being preferred.

Preferably, water is added in one portion at beginning of the reaction or can be dosed after the catalyst is activated.

The contacting step can be carried out at a temperature from about −80° C. to about 100° C., preferably −10 to 30° C., more preferably at or near room temperature, from about 1 hour to about 48 hours, preferably overnight. These conditions are generally sufficient for completion of the reaction and produce a mixture of the non-racemic chiral diol and the non-racemic chiral epoxy compound in high yield.

The cobalt based catalysts have been found to catalyze the equilibration of the regioisomers via a Smiles Rearrangement. Since internal opening of the epoxide inverts the chiral center, Smiles Rearrangement would lead to the formation of the enantiomer, eroding the enantiomeric excess (ee) of the title compound. Thus, an important advantage of the current process is that addition of a nitrogenous base, such as, ammonium hydroxide, and washing removes the cobalt catalyst, thereby preventing Smiles rearrangement and subsequent loss in ee.

When used in the presence of a co-solvent, any suitable co-solvent can be used. Preferred co-solvents include methyl tert-butyl ether (MTBE), dichloromethane, and tetrahydrofuran.

Catalyst activation in the presence of the epoxide substrate reduces operating costs and avoids the use of dichloromethane as a solvent. Electron-deficient aromatic acids as promoters reduces catalyst loads, reaction times, and increases the robustness of the reaction. The use of a base, such as, ammonium hydroxide during work-up allows ready separation of optically active epoxide and catalyst from corresponding diol, and at the same time, significantly reduces the volume of material to be processed downstream. In addition, with some epoxides the catalyst load has been reduced to approximately half of the amount required by a typical HKR process.

The present invention greatly improves the HKR reactions of epoxides by employing catalyst activation in the presence of epoxide, using electron-deficient aromatic acids as promoters, and the use of an amine, such as, ammonium hydroxide, during work-up.

Alternative work-up and isolation procedures are also possible, and will be evident to those skilled in the art.

The present invention is further described in the following examples, which are intended to be illustrative and not limiting.

EXAMPLE 1

Hydrolytic Kinetic Resolution of Styrene Oxide with (S,S)-Co(salen):

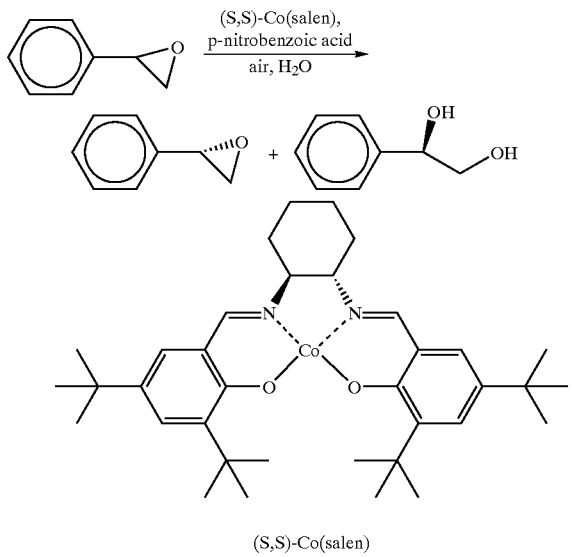

A 500-mL flask, equipped with a temperature probe, a mechanical stirrer, a vacuum adapter, and a dip tube, was charged with (S,S)-Co(salen) (5.51 g, 0.0083 mol, 0.500 mol %), styrene oxide (200.0 g, 1.66 mol, 100 mol %), and water (59.8 g, 3.32 mol, 200 mol %). A slight vacuum was applied to the flask to draw air into the reaction mixture through the dip tube (subsurface), and agitation was initiated. The flask was placed in a water bath and p-nitrobenzoic acid (2.83 g, 0.0166 mol, 1.00 mol %) was added in one portion. After stirring overnight at room temperature, the reaction was deemed complete by HPLC. The reaction mixture was a brown solution with suspended orange solids. Ammonium hydroxide (4.15 g, 4.63 mL, 28% $NH_3$, 0.0332 mol, 2.00 mol %) was added and the reaction mixture was stirred at room temperature for 1 h. A dark brown solution was obtained. Air flow through the reaction mixture was stopped, and the reaction mixture was washed with water (2×200 mL). The organic layer was fractionally distilled to give (S)-styrene oxide (67.86 g, 67.9% yield, 99.6% ee). The aqueous layer was treated with activated carbon and warmed to a gentle boil. After cooling and filtration, the aqueous layer was concentrated to give (R)-styrene glycol (95.25 g, 95.3% yield, 93.9% ee).

EXAMPLE 2

Hydrolytic Kinetic Resolution of Styrene Oxide with (R,R)-Co(salen):

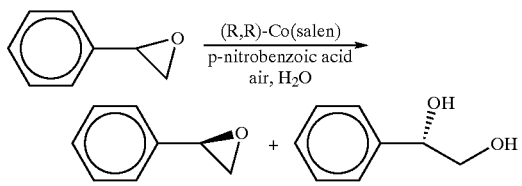

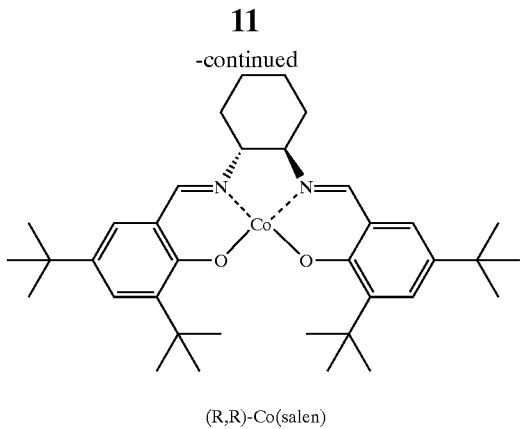

(R,R)-Co(salen)

A 500-mL flask, equipped with a temperature probe, a mechanical stirrer, a vacuum adapter, and a dip tube, was charged with (R,R)-Co(salen) (6.57 g, 0.0109 mol, 0.63 mol %), styrene oxide (209.0 g, 199.0 mL, 1.74 mol), and water (5.0 g, 5.0 mL, 0.28 mol, 16 mol %). A slight vacuum was applied to the flask to draw air into the reaction mixture through the dip tube (subsurface), agitation was initiated, and p-nitrobenzoic acid (3.64 g, 0.0218 mol, 1.25 mol %) was added in one portion. An exotherm was noted that ceased after about 3 h. When the internal temperature remained constant, additional water (5.0 g, 5.0 mL, 0.28 mol, 16 mol %) was added. An exotherm was again observed that ceased after about 1 h. This cycle was repeated two more times (2×5.0 g water). A final portion of water (42.6 g, 42.6 mL, 2.37 mol, 136 mol %) was added after the last exotherm had ceased. After stirring a total of 24 h, the reaction was deemed complete by HPLC. The reaction mixture was a brown solution with suspended orange solids. Ammonium hydroxide (3.0 mL, 28%, 0.049 mol, 2.8 mol %) was added, and the reaction mixture was stirred at room temperature for 2 h. A dark brown solution was obtained. Air flow through the reaction mixture was stopped, and the reaction mixture was washed with water (2×200 mL). The organic layer was fractionally distilled to give (R)-styrene oxide (67.0 g, 64% yield, 99.3% ee).

EXAMPLE 3

Hydrolytic Kinetic Resolution of Propylene Oxide with (S,S)-Co(salen):

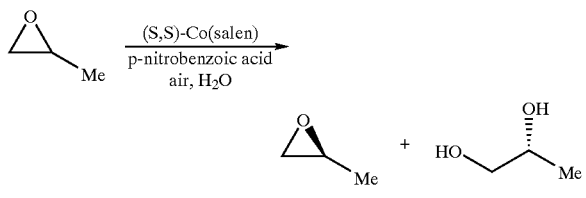

A 3-necked, 100-mL, round-bottomed flask, equipped with a temperature probe and a magnetic stirring bar was charged with (S,S)-Co(salen) catalyst (1.62 g, 0.0026 mol, 0.30 mol %). The flask was cooled with a sodium chloride/ice bath for 5 min and propylene oxide (52.29 g, 63.0 mL, 0.860 mol) was added. The resulting orange solution was cooled to less than 5° C., and p-nitrobenzoic acid (0.47 g, 0.0026 mol, 0.30 mol %) was charged. The solution was allowed to reach 20–25° C. and was stirred for 1 h under an air atmosphere. The air atmosphere was displaced by nitrogen, and the flask was cooled to 0–5° C. with an ice-bath. De-ionized water (9.76 mL, 0.520 mol, 0.60 mol %) was added dropwise over 1 h, maintaining the internal temperature below 10° C. The solution was allowed to warm to 20–25° C. and was stirred at ambient temperature until the resolution was deemed complete by GC analysis. Distillation at atmospheric pressure yielded (S)-propylene oxide (16.73 g, 80.1% yield, >99.5% ee, b.p. 34° C.). The temperature of the solution was decreased to 20–25° C., and vacuum applied, taking care not to increase the vacuum rapidly. Distillation at 1 Torr yielded (R)-propylene glycol (28.7 g, 69.9% yield, b.p. 64–65° C.).

EXAMPLE 4

Hydrolytic Kinetic Resolution of Methyl Glycidate with (R,R)-Co(salen):

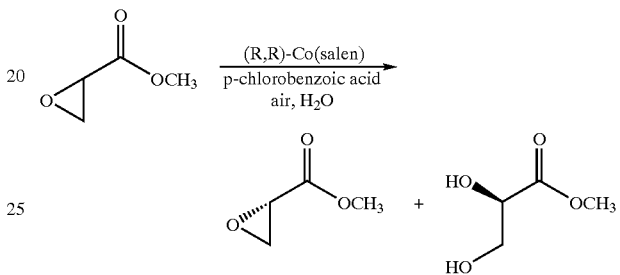

To a 500-mL flask equipped with a mechanical stirrer and a temperature probe was added in order (R,R)-Co(salen) catalyst (12.84 g, 0.0213 mol), methyl glycidate (232.0 g, 200.0 mL, 2.27 mol), 1,2-propanediol (200.0 mL) and 4-chlorobenzoic acid (6.63 g, 0.0423 mol). Agitation was initiated and the resulting solution was allowed to stir for 2 hours open to the atmosphere. Water (7.6 g, 7.6 mL, 0.422 mol, 18.6 mol %) was added, and the solution was allowed to stir until an exotherm was observed. After the internal temperature returned to room temperature, water (7.6 g, 7.6 mL, 0.422 mol, 18.6 mol %) was added. An exotherm was again observed. After the internal temperature had returned to room temperature, water (7.6 g, 7.6 mL, 0.422 mol, 18.6 mol %) was added, and the resulting solution allowed to stir for a total of 24 hours at which time GC analysis indicated the reaction was complete. Distillation gave 73.49 g of (S)-methyl glycidate (63.3% yield, >99.5% ee).

EXAMPLE 5

Preparation of (S)-3-Chloro-1,2-propanediol with (S,S)-Co(salen):

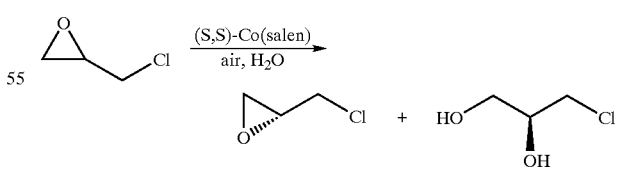

To a 3-necked, 250-mL, round-bottomed flask fitted with a vacuum adapter, an air inlet, and a temperature probe was added (S,S)-Co(salen) (1.51 g, 0.0023 mol, 0.23 mol %), propylene glycol monomethyl ether (20 mL), and p-nitrobenzoic acid (0.835 g, 0.0049 mol, 0.49 mol %). A slight vacuum was applied to pull air into the reaction medium, and the reaction was allowed to stir for 1 h. The air inlet was removed, and epichlorohydrin (92.52 g, 78.40 mL, 1.00 mol) was charged after the reaction vessel was purged with nitrogen. The reaction was cooled to 0° C., and water (8.1 g, 8.1 mL, 0.45 mol, 45 mol %) was slowly added, maintaining the reaction temperature below 5° C. The reaction was allowed to stir at room temperature for 16 h. When determined to be complete, the reaction was partitioned between toluene (80 mL) and water (80 mL). The aqueous layer was collected and washed with toluene (80 mL) to remove unreacted epichlorohydrin (isopropyl alcohol (20%) was added to facilitate the phase separation). After concentration of aqueous layer, the residue was vacuum distilled to give (S)-3-chloro-1,2-propanediol (37.4 g, 76% yield, >99% purity, 97% ee; b.p. 115–120° C. @ 10 mm Hg).

EXAMPLE 6

Comparison for acetic acid, benzoic acid and nitrobenzoic acid. A comparison of acetic acid, benzoic acid and p-nitrobenzoic acid as the counter-ion for Co(III) was performed where the mole ratio for reagents is shown in Table 1.

TABLE 1

| Styrene oxide | Co(II)(salen) | Carboxylic acid | Water |
|---|---|---|---|
| 1 | 0.008 | 0.016 | 2 |

The results are summarized in Table 2. As shown in the Table 2, when p-nitrobenzoic acid was used as the promoter, a % ee of >99.5% was achieved within only 6 hours. Such a level was never achieved when the acetic acid was employed even when the reaction was carried out over a prolonged period of time. While the performance of the benzoic acid was superior to that of acetic acid, p-nitrobenzoic acid was far superior to both acetic and benzoic acids.

TABLE 2

Enantiomer Excess[a] Obtained by Various Catalyst Promoters

| # | Time (hr) | Acetic acid | Benzoic acid | p-Nitrobenzoic acid |
|---|---|---|---|---|
| 1 | 0.5 | −0.21% | 0.15% | −0.08% |
| 2 | 1 | −0.23% | −0.05% | −0.09% |
| 3 | 1.5 | −0.35% | 0.20% | 0.35% |
| 4 | 2 | −0.14% | 0.13% | 0.25% |
| 5 | 2.5 | −0.31% | 0.57% | 12.70% |
| 6 | 3 | −0.27% | 0.43% | 49.25% |
| 7 | 3.5 | −1.21% | 0.70% | 76.06% |
| 8 | 4 | −1.14% | 0.78% | 90.26% |
| 9 | 4.5 | −1.31% | 1.20% | 95.05% |
| 10 | 5 | −1.66% | 1.60% | 97.83% |
| 11 | 5.5 | −2.04% | 1.92% | 99.08% |
| 12 | 6 | −2.09% | 3.50% | 99.59% |
| 13 | 6.5 | −2.30% | 9.24% | >99.5% |
| 14 | 7 | −2.25% | 30.27% | >99.5% |
| 15 | 7.5 | −2.72% | 58.21% | >99.5% |
| 16 | 8 | −2.98% | 80.47% | >99.5% |
| 17 | 23 | 62.32% | >99.5% | >99.5% |
| 19 | 24 | 67.03% | >99.5% | >99.5% |
| 20 | 25 | 70.51% | >99.5% | >99.5% |
| 21 | 26 | 73.76% | >99.5% | >99.5% |

[a]Enantiomeric Excess (% ee) = (S − R)/(S + R) × 100%,

EXAMPLE 7

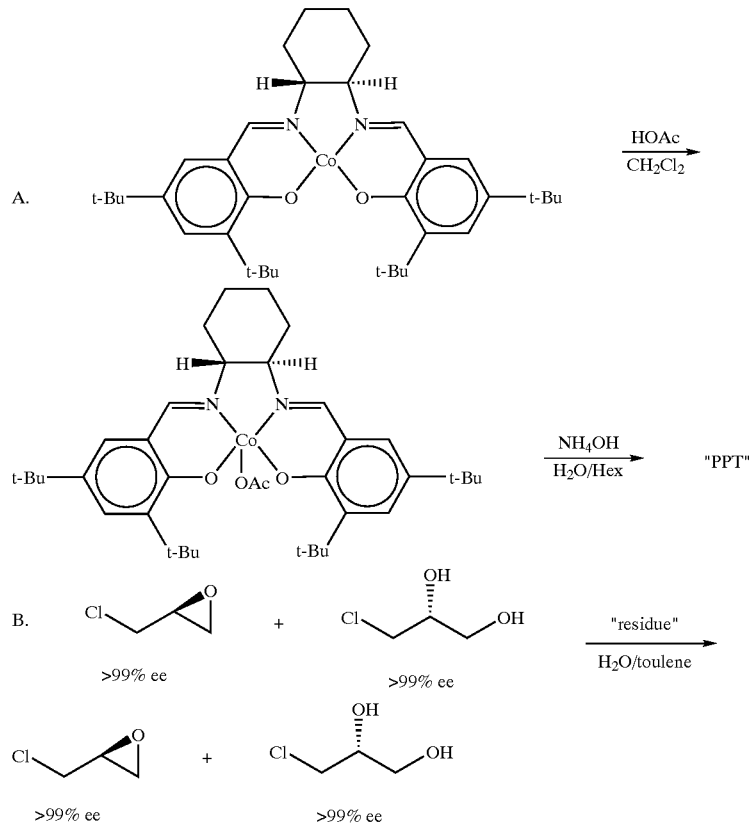

To a dry 25 mL round bottom flask, equipped with a magnetic stir bar were added the (R,R)-salen-Co$^{II}$ catalyst (0.74 g; 1.2 mmol) and dichloromethane (6 mL). Glacial acetic acid (0.12 mL; 2.2 mmol) was then added to the resulting suspension. The mixture rapidly turned homogeneous and dark brown. The dark solution was stirred in open atmosphere for one hour. The dichloromethane was removed under reduced pressure on a rotary evaporator. The furnished solid was dissolved in hexanes (6 mL) and H$_2$O (2 mL) was added and a bi-phasic mixture was obtained. To this mixture was added a 28–30% ammonium hydroxide solution (NH$_4$OH; 0.84 mL). The flask was warm to the touch and a suspension immediately formed from the mixture. The flask was placed in an ice/water bath and after ca 15 minutes a red solid resulted. The solid was filtered, washed with water and air-dried furnishing 0.894 g of the precipitate. The aqueuous solution was extracted with dichloromethane (2×5 mL) and the combined organic phases were dried over anhydrous magnesium sulfate, filtered and concentrated under reduced pressure to furnish 5 mg of a green residue, which was assumed to be activated catalyst ((R,R)-salen-Co$^{III}$-OAc).

The residue was then analyzed for activation as follows:

The residue (5 mg; 7.5 μmol) was placed in a dry 5 mL round bottom flask, equipped with a magnetic stir bar and a nitrogen inlet. Toluene (2 mL) was added and a brown solution was formed. To this solution were added a mixture of (S)-epichlorohydrin (133 mg; 1.4 mmol) and (R)-3-chloro-1,2-propanediol (158 mg; 1.4 mmol) in toluene (1 mL). To this mixture was then added H$_2$O (0.01 mL; 0.556 mmol) and the bi-phasic mixture was stirred under nitrogen atmosphere for about 15 hours. An aliquot of the mixture was analyzed and no ee erosion was observed for either (S)-epichlorohydrin or (R)-3-chloro-1,2-propanediol.

The present invention has been described with particular reference to the preferred embodiments. It should be understood that the foregoing descriptions and examples are only illustrative of the invention. Various alternatives and modifications thereof can be devised by those skilled in the art without departing from the spirit and scope of the present invention. Accordingly, the present invention is intended to embrace all such alternatives, modifications, and variations that fall within the scope of the appended claims.

What is claimed is:

1. A process for the preparation of an enantiomerically enriched non-racemic chiral diol and an enantiomerically enriched non-racemic chiral epoxy compound by a hydrolytic kinetic resolution reaction, said process comprising the step of:
   contacting oxygen and a mixture comprising a racemic chiral epoxy compound, a non-racemic Co(II) complex catalyst, an aromatic carboxylic acid and water, at a temperature and length of time sufficient to produce a mixture of said non-racemic chiral diol and said non-racemic chiral epoxy compound.

2. The process of claim 1, wherein said racemic chiral epoxy compound is represented by the formula:

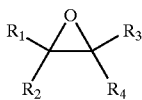

wherein each R$^1$, R$^2$, R$^3$ and R$^4$ is independently selected from the group consisting of: hydrogen, halogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, acyl, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, two or more of R$^1$, R$^2$, R$^3$ and R$^4$ together form a carbocyclic or heterocyclic 4 to 8 membered ring, and a combination thereof.

3. The process of claim 2, wherein one or more of R$^1$, R$^2$, R$^3$ and R$^4$ in said racemic chiral epoxy compound is represented by the formula:

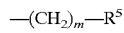

wherein R$^5$ is independently selected from the group consisting of: alkyl, cycloalkyl, cycloalkenyl, aryl, heteroaryl and heterocycle; and wherein m is zero or an integer from 1 to 8.

4. The process of claim 2, wherein said racemic chiral epoxy compound is selected from the group consisting of: styrene oxide, propylene oxide, methyl glycidate, epichlorohydrin and a mixture thereof.

5. The process of claim 1, wherein said non-racemic Co(II) complex catalyst is (S,S)-Co(II)(salen) catalyst represented by the formula:

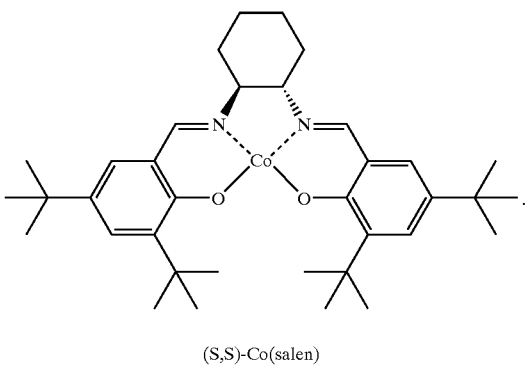

(S,S)-Co(salen)

6. The process of claim 1, wherein said non-racemic Co(II) complex catalyst is (R,R)-Co(II)(salen) catalyst represented by the formula:

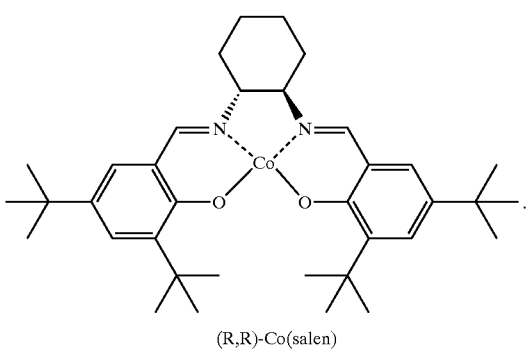

(R,R)-Co(salen)

7. The process of claim 1, wherein said non-racemic complex of Co(II) produces, in the presence of oxygen, a non-racemic complex of Co(III) having an aryl carboxylate counter-anion.

8. The process of claim 7, wherein said non-racemic complex (S,S)-Co(III) salen)(arylcarboxylate).

9. The process of claim 7, wherein said non-racemic complex (R,R)-Co(II) salen)(arylcarboxylate).

10. The process of claim 1, wherein said aromatic carboxylic acid is represented by the formula:

Ar—COOH wherein Ar is a substituted aromatic group of 1 to 24 carbon atoms having one or more substituents.

11. The process of claim 10, wherein each of said substituents is selected from the group consisting of: hydrogen, halogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, haloalkyl, haloalkenyl, haloalkynyl, heterocyclic group of 2 to 7 carbon atoms containing one or more of oxygen, nitrogen or sulfur, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, nitro, fluoro, cyano, acyl, imine, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, tertiary amine cation and a combination thereof.

12. The process of claim 11, wherein said substituted aromatic group is an electron deficient substituted aromatic group having one or more electron withdrawing substituents.

13. The process of claim 12, wherein each of said electron withdrawing substituents is selected from the group consisting of: nitro, fluoro, chloro, bromo, cyano, acyl, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation and a combination thereof.

14. The process of claim 10, wherein said aromatic carboxylic acid is selected from the group consisting of: nitrophenyl, dinitrophenyl, trinitrophenyl, chlorophenyl, dichlorophenyl, trichlorophenyl, tetrachlorophenyl, pentachlorophenyl, fluorophenyl, difluorophenyl, trifluorophenyl, tetrafluorophenyl, pentafluorophenyl, cyanophenyl, dicyanophenyl, tricyanophenyl and a combination thereof.

15. The process of claim 10, wherein said aromatic carboxylic acid is represented by the formula:

$R^6$—$C_6H_4$—COOH wherein $R^6$ is selected from the group consisting of: nitro, fluoro, chloro, cyano, acyl, alkoxycarbonyl, aryloxycarbonyl, aminocarbonyl, alkanesulfonyl, arylsulfonyl, perfluoroalkanesulfonyl, perfluoroarylsulfonyl, tertiary amine cation and a combination thereof.

16. The process of claim 1, wherein said non-racemic chiral diol is selected from the group consisting of a compound represented by the formula:

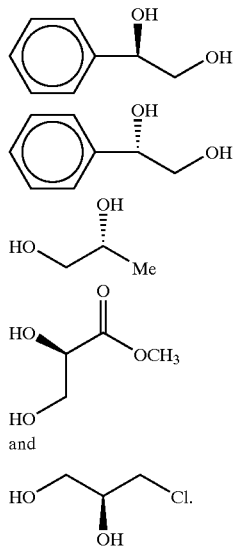

and

17. The process of claim 1, wherein said non-racemic chiral epoxy compound is selected from the group consisting of a compound represented by the formula:

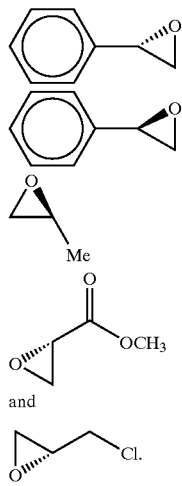

and

18. The process of claim 1, wherein said contacting is carried out at room temperature.

19. The process of claim 1, wherein said contacting is carried out for length of time from about 1 hour to about 48 hours.

20. The process of claim 1, further comprising contacting said mixture and a nitrogenous base to produce a solution of said mixture.

21. The process of claim 20, wherein said nitrogenous base is selected from the group consisting of an amine, an amidine, a guanidine, imidate ester, ammonium hydroxide, hydroxyamine and a combination thereof.

22. The process of claim 21, wherein said amine is represented by the formula:

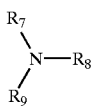

wherein each $R^7$, $R^8$ and $R^9$ is independently selected from the group consisting of: hydrogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, hydroxyalkyl, aminoalkyl, alkylaminoalkyl, dialkylaminoalkyl, aminoaryl, alkylaminoaryl, dialkylaminoaryl, trialkylsilyl, alkyl ether, aryl ether, alkyl aryl ether, two or more of $R^7$, $R^8$ and $R^9$ together form a carbocyclic or heterocyclic 4 to 8 membered ring, and a combination thereof.

23. The process of claim 20, further comprising washing said solution of said mixture with water to separate said non-racemic chiral diol from said non-racemic chiral epoxy compound as an aqueous solution thereof.

24. The process of claim 23, further comprising distilling said non-racemic chiral epoxy compound to produce said enantiomerically enriched non-racemic chiral epoxy compound in high regioselectivity and enantioselectivity.

25. The process of claim 24, further comprising concentrating said aqueous solution of non-racemic chiral diol to produce said enantiomerically enriched non-racemic chiral diol in high regioselectivity and enantioselectivity.

26. A process for the preparation of an enantiomerically enriched non-racemic chiral diol and an enantiomerically enriched non-racemic chiral epoxy compound by a hydrolytic kinetic resolution reaction, said process comprising the step of:

contacting a racemic chiral epoxy compound and water in the presence of a non-racemic complex of Co(III) having an aryl carboxylate counter-anion substituted by one or more electron withdrawing groups, wherein said contacting is carried out at a temperature and length of time sufficient to produce a mixture of said non-racemic chiral diol and said non-racemic chiral epoxy compound.

27. The process of claim 26, wherein said racemic chiral epoxy compound is represented by the formula:

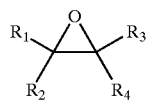

wherein each $R^1$, $R^2$, $R^3$ and $R^4$ is independently selected from the group consisting of: hydrogen, halogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, acyl, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, two or more of $R^1$, $R^2$, $R^3$ and $R^4$ together form a carbocyclic or heterocyclic 4 to 8 membered ring, and a combination thereof.

28. The process of claim 27, wherein one or more of $R^1$, $R^2$, $R^3$ and $R^4$ in said racemic chiral epoxy compound is represented by the formula:

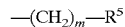

wherein $R^5$ is independently selected from the group consisting of: alkyl, cycloalkyl, cycloalkenyl, aryl, heteroaryl and heterocycle; and wherein m is zero or an integer from 1 to 8.

29. The process of claim 27, wherein said racemic chiral epoxy compound is selected from the group consisting of: styrene oxide, propylene oxide, methyl glycidate, epichlorohydrin and a mixture thereof.

30. The process of claim 26, wherein said non-racemic complex of Co(III) having an aryl carboxylate counter-anion is (S,S)-Co(III)(salen)-(arylcarboxylate) catalyst.

31. The process of claim 26, wherein said non-racemic complex of Co(III) having an aryl carboxylate counter-anion is (R,R)-Co(III)(salen)-(arylcarboxylate) catalyst.

32. The process of claim 26, wherein said aryl carboxylate counter-anion is the counter-anion of an aromatic carboxylic acid represented by the formula:

wherein Ar is a substituted aromatic group having one or more electron withdrawing substituents.

33. The process of claim 32, wherein each of said electron withdrawing substituents is selected from the group consisting of: halogen, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, alkaryl of 7 to 22 carbon atoms, haloalkyl, haloalkenyl, haloalkynyl, heterocyclic group of 2 to 7 carbon atoms containing one or more of oxygen, nitrogen or sulfur, alkyl ketone, aryl ketone, alkyl aryl ketone, aldehyde, alkoxycarbonyl, aryloxycarbonyl, alkyl ester, aryl ester, alkyl aryl ester, hydroxyalkyl, hydroxyaryl, carboxyalkyl, carboxyaryl, aminoalkyl, alkylaminoalkyl, dialkylaminoalkyl, aminoaryl, alkylaminoaryl, dialkylaminoaryl, nitroalkyl, nitroaryl, thioalkyl, thioaryl, amidoalkyl, amidoaryl, trialkylsilyl, trialkoxysilyl, triarlyoxysilyl, alkylsulfonyl, arylsulfonyl, alkyl sulfone, aryl sulfone, alkylaryl sulfone, alkyl ether, aryl ether, alkyl aryl ether, alkylthioether, arylthioether, selenoether, phosphoryl, phosphate, phosphonate, phosphine, phosphine oxide, nitro, fluoro, cyano, acyl, imine, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, tertiary amine cation and a combination thereof.

34. The process of claim 33, wherein said substituted aromatic group is an electron deficient substituted aromatic group having one or more electron withdrawing substituents.

35. The process of claim 34, wherein each of said electron withdrawing substituents is selected from the group consisting of: nitro, fluoro, chloro, bromo, cyano, acyl, carboxylic, alkoxycarbonyl, aryloxycarbonyl, aminocarbonyl, sulfonic, alkanesulfonyl, arylsulfonyl, perfluoroalkanesulfonyl, perfluoroarylsulfonyl, phosphoryl, tertiary amine cation and a combination thereof.

36. The process of claim 32, wherein said aromatic carboxylic acid is selected from the group consisting of: nitrophenyl, dinitrophenyl, trinitrophenyl, chlorophenyl, dichlorophenyl, trichlorophenyl, tetrachlorophenyl, pentachlorophenyl, fluorophenyl, difluorophenyl, trifluorophenyl, tetrafluorophenyl, pentafluorophenyl, cyanophenyl, dicyanophenyl, tricyanophenyl and a combination thereof.

37. The process of claim 32, wherein said aromatic carboxylic acid is represented by the formula:

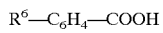

R$^6$—C$_6$H$_4$—COOH wherein R$^6$ is selected from the group consisting of: nitro, fluoro, chloro, cyano, acyl, alkoxycarbonyl, aryloxycarbonyl, aminocarbonyl, alkanesulfonyl, arylsulfonyl, perfluoroalkanesulfonyl, perfluoroarylsulfonyl, tertiary amine cation and a combination thereof.

38. The process of claim 26, wherein said non-racemic chiral diol is selected from the group consisting of a compound represented by the formula:

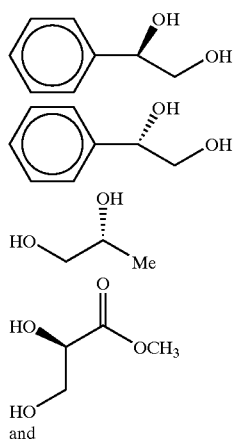

and

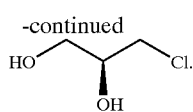

39. The process of claim 26, wherein said non-racemic chiral epoxy compound is selected from the group consisting of a compound represented by the formula:

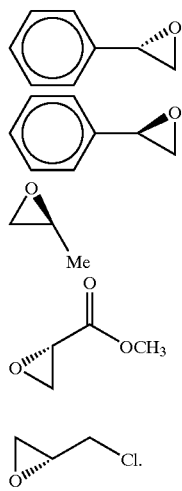

and

40. The process of claim 26, wherein said contacting is carried out for length of time from about 1 hour to about 48 hours.

41. The process of claim 26, further comprising contacting said mixture and a nitrogenous base to produce a solution of said mixture.

42. The process of claim 41, wherein said nitrogenous base is selected from the group consisting of an amine, an amidine, a guanidine, imidate ester, ammonium hydroxide, hydroxyamine and a combination thereof.

43. The process of claim 42, wherein said amine is represented by the formula:

$$\begin{array}{c} R_7 \\ \diagdown \\ N{\rm —}R_8 \\ \diagup \\ R_9 \end{array}$$

wherein each R$^7$, R$^8$ and R$^9$ is independently selected from the group consisting of: hydrogen, linear, branched or cyclic alkyl of 1 to 22 carbon atoms, linear, branched or cyclic alkenyl of 2 to 22 carbon atoms, linear, branched or cyclic alkynyl of 2 to 22 carbon atoms, aryl of 6 to 22 carbon atoms, heteroaryl of 6 to 22 carbon atoms, aralkyl of 7 to 22 carbon atoms, alkaryl of 7 to 22 carbon atoms, heterocyclic group of 2 to 7 carbon atoms containing one or more of oxygen, nitrogen or sulfur, imino, hydroxyalkyl, aminoalkyl, alkylaminoalkyl, dialkylaminoalkyl, aminoaryl, alkylaminoaryl, dialkylaminoaryl, trialkylsilyl, alkyl ether, aryl ether, alkyl aryl ether, two or more of R$^7$, R$^8$ and R$^9$ together form a carbocyclic or heterocyclic 4 to 8 membered ring, and a combination thereof.

44. The process of claim 41, further comprising washing said solution of said mixture with water to separate said non-racemic chiral diol from said non-racemic chiral epoxy compound as an aqueous solution thereof.

45. The process of claim 41, further comprising distilling said non-racemic chiral epoxy compound to produce said enantiomerically enriched non-racemic chiral epoxy compound in high regioselectivity and enantioselectivity.

46. The process of claim 41, further comprising concentrating said aqueous solution of non-racemic chiral diol to produce said enantiomerically enriched non-racemic chiral diol in high regioselectivity and enantioselectivity.

47. A process for the preparation of an enantiomerically enriched non-racemic chiral diol and an enantiomerically enriched non-racemic chiral epoxy compound by a hydrolytic kinetic resolution reaction, said process comprising the steps of:

contacting: (a) oxygen and a mixture comprising a racemic chiral epoxy compound, a non-racemic Co(II) complex catalyst, an aromatic carboxylic acid and water; or (b) a racemic chiral epoxy compound and water in the presence of a non-racemic complex of Co(III) having an aryl carboxylate counter-anion; wherein said contacting is carried out at a temperature and length of time sufficient to produce a mixture of said non-racemic chiral diol and said non-racemic chiral epoxy compound;

contacting said mixture and a nitrogenous base to produce a solution of said mixture; and washing said solution of said mixture with water to separate said non-racemic chiral diol from said non-racemic chiral epoxy compound as an aqueous solution thereof.

48. The process of claim 47, further comprising:

distilling said non-racemic chiral epoxy compound to produce said enantiomerically enriched non-racemic chiral epoxy compound in high regioselectivity and enantioselectivity.

49. The process of claim 48, further comprising:

concentrating said aqueous solution of non-racemic chiral diol to produce said enantiomerically enriched non-racemic chiral diol in high regioselectivity and enantioselectivity.

50. A non-racemic chiral epoxy compound or diol having a high regioselectivity and enantioselectivity prepared by the process of claim 1.

51. A non-racemic chiral epoxy compound or diol having a high regioselectivity and enantioselectivity prepared by the process of claim 26.

52. A non-racemic chiral epoxy compound or diol having a high regioselectivity and enantioselectivity prepared by the process of claim 47.

53. A process for the preparation of an enantiomerically enriched non-racemic chiral diol and an enantiomerically enriched non-racemic chiral epoxy compound by a hydrolytic kinetic resolution reaction, said process comprising the steps of:

contacting oxygen and a mixture comprising a racemic chiral epoxy compound, a non-racemic Co(II) complex catalyst, a carboxylic acid and water, at a temperature and length of time sufficient to produce a mixture of said non-racemic chiral diol and said non-racemic chiral epoxy compound; and contacting said mixture and a nitrogenous base to produce a solution of said mixture.

54. The process of claim 53, wherein said nitrogenous base is selected from the group consisting of an amine, an amidine, a guanidine, imidate ester, ammonium hydroxide, hydroxyamine and a combination thereof.

55. A process for the preparation of an enantiomerically enriched non-racemic chiral diol and an enantiomerically enriched non-racemic chiral epoxy compound by a hydrolytic kinetic resolution reaction, said process comprising the steps of:

contacting a racemic chiral epoxy compound and water in the presence of a non-racemic complex of Co(III) having an a carboxylate counter-anion, at a temperature and length of time sufficient to produce a mixture of said non-racemic chiral diol and said non-racemic chiral epoxy compound; and contacting said mixture and a nitrogenous base to produce a solution of said mixture.

56. The process of claim 55, wherein said nitrogenous base is selected from the group consisting of an amine, an amidine, a guanidine, imidate ester, ammonium hydroxide, hydroxyamine and a combination thereof.

* * * * *